(12) United States Patent
Liang et al.

(10) Patent No.: US 6,429,339 B1
(45) Date of Patent: Aug. 6, 2002

(54) METHOD FOR PRODUCING CYCLOPENTANONE

(75) Inventors: Shelue Liang, Ludwigshafen; Rolf Fischer, Heidelberg; Frank Stein, Bad Dürkheim; Joachim Wulff-Döring, Frankenthal, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/700,365

(22) PCT Filed: May 10, 1999

(86) PCT No.: PCT/EP99/03194

§ 371 (c)(1),
(2), (4) Date: Nov. 15, 2000

(87) PCT Pub. No.: WO99/61402

PCT Pub. Date: Dec. 2, 1999

(30) Foreign Application Priority Data

May 28, 1998 (DE) .......................................... 198 23 835

(51) Int. Cl.$^7$ .............................................. C07C 45/00
(52) U.S. Cl. ........................ 568/355; 568/314; 568/397
(58) Field of Search ................................ 568/355, 397, 568/314

(56) References Cited

U.S. PATENT DOCUMENTS 2,863,923 A    12/1958    Bortnick 4,048,244 A  *  9/1977    Hayes
4,745,228 A    5/1988     Decker
4,822,920 A    4/1989     Lermer

FOREIGN PATENT DOCUMENTS

DE    36 38 005    5/1988
EP    251 111      1/1988

* cited by examiner

Primary Examiner—Sreeni Padmanabhan
Assistant Examiner—Sikarl A. Witherspoon
(74) Attorney, Agent, or Firm—Keil & Weinkauf

(57) ABSTRACT

A process for preparing cyclopentanone by reacting adipic esters of the formula $$R_1OOC-(CH_2)_4-COOR_2 \qquad I$$

where $R_1$ and $R_2$ are each alkyl having from 1 to 12 carbon atoms, cycloalkyl having 5 or 6 carbon atoms, aralkyl or aryl and $R_2$ may additionally be hydrogen, in the presence of oxidic catalysts comprises reacting adipic esters of the formula I having less than 5% by weight of by-products other than adipic esters in the gas phase in the presence of water, a carrier gas and a) from 0.01 to 10% by weight of at least one metal oxide selected from the first or second main group of the periodic table or from the group of the rare earth metals on titanium dioxide or zirconium dioxide as catalyst support, or b) from 0.01 to 50% by weight of at least one metal oxide selected from the second main group of the periodic table on zink oxide as catalyst support.

12 Claims, No Drawings

METHOD FOR PRODUCING CYCLOPENTANONE

This invention relates to an improved process for preparing cyclopentanone by reacting adipic esters in the gas phase over oxidic fixed bed catalysts.

U.S. Pat. No. 2,863,923 discloses preparing 2,5-dialkylcyclopentanones by heating 2,5-dialkyladipic diesters in the gas phase in the presence of metal oxides whose metal component has atomic weights between 7 and 137. The most effective catalysts are said to be the oxides of sodium, of potassium, of lithium, of calcium, of barium, of strontium, of cadmium, of zinc, of manganese, of copper, of iron, of nickel and of cobalt. Particular preference is given to the oxides of manganese, of cadmium and of sodium. Suitable catalyst supports are $Al_2O_3$, $SiO_2$ and activated carbon. The reaction is carried out at from 350 to 600° C., preferably 400 to 475° C. The process is carried out without water and without carrier gas. In the operative examples, dimethyl 2,5-dimethyladipate is reacted over an $MnO_2/Al_2O_3$ catalyst at 435 to 465° C. Further examples are carried out using $CdO/Al_2O_3$, $Na_2O/Al_2O_3$ and $ZnO/Al_2O_3$ (no data are given for catalyst composition) in the temperature range from 375 to 502° C. Nothing is said about the 2,5-dimethylcyclopentanone yields.

EP 251 111 A2 discloses converting aliphatic dicarboxylic esters having from six to eight carbon atoms in the chain into the corresponding cycloalkanones by adding water and using carrier gases.

The catalysts used are solid oxidic catalysts. Examples include oxides of elements of the Ist to Vth main group, of the Ist to VIIIth transition group of the periodic table of the elements or oxides of the rare earth metals or mixtures thereof. Suitable examples are alkaline earth metal oxides, such as magnesium oxide, calcium oxide, barium oxide, also boron trioxide, aluminum oxide, silicon dioxide, for example in the form of silica gel, kieselguhr, or quartz, also tin dioxide, bismuth oxide, copper oxide, zinc oxide, lanthanum oxide, titanium dioxide, zirconium dioxide, vanadium oxides, chromium oxides, molybdenum oxides, tungsten oxides, manganese oxides, iron oxides, cerium oxides, neodymium oxides or mixtures thereof. The catalysts can be modified by application of additaments, such as acids (e.g., phosphoric acid) or bases (e.g., sodium hydroxide). Preference is given to magnesium oxide, boron trioxide, aluminum oxide, silicon dioxide, zinc oxide, titanium dioxide or mixtures thereof, of which aluminum oxide catalysts are very particularly suitable.

The highest cyclopentanone selectivities are obtained in Operative Examples 2.1 and 2.7. Example 2.1 involves dimethyl adipate being reacted at 340° C. over a fixed bed of γ-alumina to form cyclopentanone with 88% selectivity (and a yield of 74%), while Example 2.7 involves dimethyl adipate being reacted at 400° C. over $Li_2O$ (13.5%)/MgO, giving cyclopentanone with 91% selectivity (yield 62%).

DE-A 36 37 787 discloses converting suberic diesters into cycloheptanone by reaction in the gas phase over oxidic catalysts in the presence of water or alcohols at from 300 to 600° C., preferably 400 to 500° C. The catalysts used are 5 to 35%, especially 8 to 20%, of zinc oxide or cerium oxide on alumina. The highest cycloheptanone selectivity is obtained in Example 5, where dimethyl suberate is reacted at 440° C. over 12% of ZnO on $Al_2O_3$ in the presence of methanol to form cycloheptanone with 76% selectivity and 49% yield.

It is an object of the present invention to further improve the process for preparing cyclopentanone from adipic esters, especially with regard to the cyclopentanone selectivity, by providing still better catalysts. A high cyclopentanone selectivity shall be coupled with a very high cyclopentanone yield in order to minimize the need for an adipic ester recycle. Furthermore, the catalysts shall have a long onstream life.

We have found that this object is achieved by a process for preparing cyclopentanone by reacting adipic esters having an adipic ester content of more than 95%, preferably more than 97%, especially within the range from 98.5 to 100% by weight, of the formula

$$R_1OOC-(CH_2)_4-COOR_2 \qquad I$$

where $R_1$ and $R_2$ are each alkyl having from 1 to 12 carbon atoms, cycloalkyl having 5 or 6 carbon atoms, aralkyl or aryl and $R_2$ may additionally be hydrogen, in the presence of oxidic catalysts, which comprises conducting the reaction in the gas phase in the presence of water, a carrier gas and a) from 0.01 to 10% by weight of at least one metal oxide selected from the first or second main group of the periodic table or from the group of the rare earth metals on titanium dioxide or zirconium dioxide as catalyst support, or b) from 0.01 to 50% by weight of at least one metal oxide selected from the second main group of the periodic table on zinc oxide as catalyst support.

The reaction can be carried out not only in the gas phase but also, less advantageously, in the liquid phase, if appropriate even in the presence of diluents. Examples of suitable diluents include solvents which are completely or substantially inert under the reaction conditions, for example ethers such as dioxane or tetrahydrofuran.

The starting esters of the formula I are aliphatic, cycloaliphatic or aromatic mono- or diesters of adipic acid. Examples of $R_1$ and $R_2$ are methyl, ethyl, propyl, isopropyl, butyl, isobutyl, tert-butyl, hexyl, nonyl, dodecyl, cyclopentyl, cyclohexyl, phenyl and benzyl. Methyl is particularly preferred.

Examples of esters which can be used as starting materials include dimethyl adipate, methyl hydrogen adipate, diethyl adipate, dibutyl adipate, dicyclohexyl adipate, dibenzyl adipate and ethyl hydrogen adipate.

One particular embodiment comprises using adipic diesters comprising small amounts of 6-hydroxycaproic ester, as obtainable for example by the processes described in DE-A 19 607 954, in which case small amounts of further compounds such as caprolactone, 6-alkoxycaproic ester, glutaric diester, 5-hydroxyvaleric ester, 2-oxocaproic ester, 1,2-cylohexanediols, valerolactone, unsaturated adipic diesters such as, for example, dihydromuconic diester, 3-hydroxypentanoic ester, 4-oxopentanoic ester and 5-oxohexanoic ester may be present. Surprisingly, these compounds generally neither impair the reaction of the invention nor lead to inferior product quality following distillative purification.

In general, total impurities are within the range from 0.01 to 4.5% by weight, especially within the range from 0.1 to 3% by weight (based on adipic diester).

True, it is possible to carry out the reaction of the invention without the addition of water, but the addition of water brings about a remarkable increase in selectivity and onstream life. The molar ratio of ester (I) to water is advantageously within the range from 1:0.05 to 1:30, especially within the range from 1:0.1 to 1:15.

It may also be advantageous to add additional alcohols such as, for example, methanol, ethanol, n-butanol, isopropanol, n-propanol. Here it is advantageous to use alcohols which form the basis of the esters (I). The molar ratios of ester (I) to alcohol correspond to those mentioned for the addition of water.

The carrier gases used are gases which are inert under the reaction conditions, for example, nitrogen, argon or carbon dioxide. The molar ratio of ester of the formula (I) to inert gas is within the range from 1:1 to 1:100, especially within the range from 1:10 to 1:50, preferably within the range from 1:20 to 20 1:40.

Catalysts (a) are metal oxides of the first and second main groups of the periodic table or of the group of the rare earth metals on titanium dioxide or zirconium dioxide as catalyst support.

Examples of such metal oxides are sodium oxide, lithium oxide, potassium oxide, calcium oxide, magnesium oxide, lanthanum oxide, cerium oxide, praseodymium oxide, neodymium oxide. Particular preference is given to sodium oxide, potassium oxide and lanthanum oxide.

The amount of metal oxide on the catalyst support is within the range from 0.01 to 10% by weight, preferably within the range from 0.1 to 5% by weight, particularly preferably within the range from 0.1 to 3% by weight, of metal oxide.

The titanium oxide has a surface area of from 20 to 200 m$^2$/g and consists predominantly of anatase. The preparation of such catalysts is described in EP-A 352 674.

Catalyst (b) is a metal oxide of the second main group of the periodic table on zinc oxide as catalyst support.

Examples of such metal oxides are magnesium oxide, calcium oxide, strontium oxide and barium oxide. Particular preference is given to magnesium oxide and calcium oxide. The amount of metal oxide on the catalyst support is within the range from 1 to 50% by weight.

The reaction in the presence of catalysts (a) takes place at from 220 to 350° C., preferably at from 230 to 330° C., particularly preferably at from 250 to 310° C., and that of catalysts (b) at from 300 to 450° C., preferably at from 330 to 420° C., particularly preferably at from 350 to 400° C.

In general, the reaction is carried out under atmospheric pressure. However, it is also possible to employ slightly reduced or slightly elevated pressure, for example up to 20 bar. The weight hourly space velocity is generally within the range from 0.01 to 40, preferably from 0.1 to 20, g of ester (I) per gram of catalyst per hour.

It is also possible in principle to carry out the reaction less advantageously in the liquid phase using fixed bed catalysts or suspended catalysts. However, it is preferred to carry out the process of the invention in the gas phase. In this case, fixed bed catalysts are preferred, since fluidized bed catalysts are more complicated to use and prone to catalyst losses.

The preferred reaction in the gas phase is carried out for example by passing a mixture of ester (I) and water into a vaporizer and from there with a carrier gas over the fixed bed catalyst at the desired temperature. The reaction mixture is condensed and subjected to fractional distillation to recover cyclopentanone. Unconverted ester (I) is removed and recycled into the cyclopentanone synthesis step.

The fixed bed catalysts to be used according to the present invention provide higher cyclopentanone yields coupled with high cyclopentanone selectivities than described in EP-A 251 111.

EXAMPLES

The percentages reported to characterize the catalysts are by weight.

a) Preparation of Catalysts $ZrO_2$: from Norton (SN 951 6321), used directly as such.

$La_2O_3$(3% of La)/$ZrO_2$: $ZrO_2$ (Norton SN 951 6321) was impregnated with $La(NO_3)_3$ solution, dried at 120° C. for four hours and calcined at 400° C. for six hours.

44% of CaO/56% of ZnO: from BASF (H 5-11)

b) Experimental Procedure for Examples in Table 1

In an electrically heated gas phase reactor, in each case 100 ml of catalyst were overlaid with 30 ml of quartz rings as vaporizer zone. From 10 to 15 g per hour of the adipic ester mentioned in the table were passed downward over the catalyst together with water and nitrogen under the stated conditions. The reaction effluents were condensed in a receiver cooled with dry ice/acetone. On the basis of the reaction effluent collected over a period of seven hours, analysis by gas chromatography revealed the following cyclopentanone yields and selectivities (based on dimethyl adipate used):

Cyclopentanone from Dimethyl Adipate

| Example | Starting material I | Catalyst | Catalyst space velocity [kg of I/$_{liter}$ of cat x h] | Molar ratio of I: $H_2O:N_2$ | Temperature [° C.] | Cyclopentanone yield [%] | Cyclopentanone selectivity [%] |
|---|---|---|---|---|---|---|---|
| 1 | Dimethyl adipate (98.7% pure) | H 5–11 | 0.1 | 1:6:10 | 370 | 90.0 | 91.7 |
| 2 | | $La_2O_3$ (3% of La)/$ZrO_2$ | 0.1 | 1:10:10 | 300 | 82.3 | 84.0 |
| 3 (comparative) | | $ZrO_2$ | 0.1 | 1:5:10 | 350 | 6.5 | 6.6 |
| 4 | | $K_2O$ (2%)/$TiO_2$ | 0.15 | 1:10:25 | 270 | 77.3 | 93.5 |
| 5 (comparative) | | $TiO_2$ | 0.10 | 1:6:10 | 250 | 56.9 | 73.1 |

Example 6

In an electrically heated gas phase reactor, 50 ml of $K_2O/TiO_2$ catalyst (2% by weight of $K_2O$, from BASF) were overlaid with 20 ml of quartz rings as vaporizer zone. Per hour, 7.5 g of dimethyl adipate and 7.5 g of water were metered in separately, and 25 standard L of nitrogen were passed in, at 270° C. and atmospheric pressure. The reaction effluents were condensed in a receiver cooled with dry ice/acetone. A total of 4774 g of effluent was collected over 408 hours. GC analysis using an internal standard revealed 12.2% by weight of dimethyl adipate and 24.0% by weight of cyclopentanone. The dimethyl adipate conversion was 81 mol %, the cyclopentanone yield was 77.6 mol % and the cyclopentanone selectivity was 95.8 mol %.

We claim:

1. A process for preparing cyclopentanone by reacting adipic esters of the formula

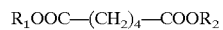

$R_1OOC-(CH_2)_4-COOR_2$ where $R_1$ and $R_2$ are each alkyl having from 1 to 12 carbon atoms, cycloalkyl having 5 or 6 carbon atoms, aralkyl or aryl and $R_2$ may additionally be hydrogen, in the presence of oxidic catalysts, which comprises reacting adipic esters of the formula I having less than 5% by weight of by-products other than adipic esters in the gas phase in the presence of water, a carrier gas and
   a) from 0.01 to 10% by weight of at least one metal oxide selected from the first or second main group of the periodic table or from the group of the rare earth metals on titanium dioxide or zirconium dioxide as catalyst support, or
   b) from 0.01 to 50% by weight of at least one metal oxide selected from the second main group of the periodic table on zinc oxide as catalyst support.

2. A process as claimed in claim 1, wherein the starting material used is an adipic ester of the formula I comprising a total of from 0.01 to 4.5% by weight of hydroxycaproic ester and caprolactone.

3. A process as claimed in claim 1, wherein the starting material used is an adipic ester of the formula I comprising a total of from 0.1 to 3% by weight of hydroxycaproic ester and caprolactone.

4. A process as claimed in claim 1, wherein the reaction is carried out in the presence of water using a molar ratio of adipic ester to water within the range from 1:0.05 to 1:30.

5. A process as claimed in claim 1, wherein the catalyst used is selected from the group consisting of sodium oxide, potassium oxide or lanthanum oxide on the supports titanium dioxide or zirconium dioxide, and magnesium oxide or calcium oxide on zinc oxide as support.

6. A process as claimed in claim 1, wherein the reaction is carried out in the presence of catalysts (a) and at from 220 to 350° C.

7. A process as claimed in claim 1, wherein the reaction is carried out in the presence of catalysts (b) and at from 300 to 450° C.

8. A process as claimed in claim 1, wherein the reaction is carried out in the presence of one or more catalysts (a).

9. A process as claimed in claim 8, wherein the starting material used is an adipic ester of the formula I comprising a total of from 0.01 to 4.5% by weight of hydroxycaproic ester and caprolactone.

10. A process as claimed in claim 8, wherein the starting material used is an adipic ester of the formula I comprising a total of from 0.1 to 3% by weight of hydroxycaproic ester and caprolactone.

11. A process as claimed in claim 8, wherein the reaction is carried out in the presence of water using a molar ratio of adipic ester to water of from 1:0.05 to 1:30.

12. A process as claimed in claim 8, wherein the metal oxide is selected from the group consisting of sodium oxide, potassium oxide and lanthanum oxide.

* * * * *